United States Patent
Leavitt et al.

(10) Patent No.: US 9,920,883 B2
(45) Date of Patent: Mar. 20, 2018

(54) DAMAGE INDICATOR FOR A COMPOSITE PRESSURE TANK

(71) Applicant: Quantum Fuel Systems LLC, Lake Forest, CA (US)

(72) Inventors: Mark Leavitt, Laguna Hills, CA (US); Mohit Garg, Lake Forest, CA (US); David Rea, Irvine, CA (US)

(73) Assignee: Quantum Fuel Systems LLC, Lake Forest, CA (US)

( * ) Notice: Subject to any disclaimer, the term of this patent is extended or adjusted under 35 U.S.C. 154(b) by 583 days.

(21) Appl. No.: 14/452,434

(22) Filed: Aug. 5, 2014

(65) Prior Publication Data

US 2016/0010802 A1    Jan. 14, 2016

Related U.S. Application Data

(60) Provisional application No. 62/023,130, filed on Jul. 10, 2014.

(51) Int. Cl.
| | |
|---|---|
| *F21V 9/16* | (2006.01) |
| *F17C 13/02* | (2006.01) |
| *F17C 13/00* | (2006.01) |
| *G01N 21/88* | (2006.01) |

(52) U.S. Cl.
CPC ............ *F17C 13/02* (2013.01); *F17C 13/003* (2013.01); *G01N 21/8803* (2013.01); *F17C 2203/0604* (2013.01); *F17C 2203/0607* (2013.01); *F17C 2203/0609* (2013.01); *F17C 2203/0626* (2013.01); *F17C 2203/0663* (2013.01); *G01N 2201/061* (2013.01)

(58) Field of Classification Search
CPC ..... G08B 13/186; G08B 13/04; G08B 13/124
USPC ........................ 340/555; 250/227.15, 227.16
See application file for complete search history.

(56) References Cited

U.S. PATENT DOCUMENTS

| | | |
|---|---|---|
| 5,476,189 A | 12/1995 | Duvall et al. |
| 2003/0129300 A1 | 7/2003 | Okada et al. |
| 2005/0180677 A1 | 8/2005 | Andrews et al. |
| 2008/0149636 A1 | 6/2008 | Carter et al. |
| 2012/0094099 A1 | 4/2012 | Hong |
| 2013/0007999 A1 | 1/2013 | Sen et al. |
| 2013/0105501 A1* | 5/2013 | Vanswijgenhoven . B29C 53/581 220/660 |

FOREIGN PATENT DOCUMENTS

| | | |
|---|---|---|
| EP | 1489350 | 12/2004 |
| EP | 2537666 | 12/2012 |

OTHER PUBLICATIONS

International Patent Application No. PCT/US2015/039257; Int'l Search Report and the Written Opinion; dated Sep. 30, 2015; 16 pages.

(Continued)

*Primary Examiner* — Kenneth J Malkowski
(74) *Attorney, Agent, or Firm* — Baker & Hostetler LLP (57) ABSTRACT

A composite fuel tank, formed by winding filaments or strips around a plastic liner and binding the material with a curable binder. Embedded within the wrapped material at predetermined depths from the surface which provides a color indication of the level of damage due to tears, gashes, cuts and the like. The color indicator is part of a visual inspection method to determine tank damage and the extent of repair necessary.

12 Claims, 5 Drawing Sheets

(56) References Cited

OTHER PUBLICATIONS

International Patent Application No. PCT/US2015/039257; Int'l Preliminary Report on Patentability; dated Jan. 19, 2017; 13 pages.
Supplementary European Search Report dated Jan. 18, 2018, issued in European Patent Application 15818177.3.

* cited by examiner

DAMAGE INDICATOR FOR A COMPOSITE PRESSURE TANK

RELATED APPLICATION

This application claims benefit from the provisional patent application 62/023,130 filed on Jul. 10, 2014, which is incorporated in its entirety by reference.

BACKGROUND

1. Field

This disclosure relates to an embedded visual inspection device and method to assess the extent of damage to a composite pressurized gas tank.

2. General Background

Motor vehicles may be fueled by gaseous fuels. Gaseous fuels are traditionally stored bound too chemical hydrides under low pressure or under higher pressure in tank structures. In transportation the weight of a vehicle, including fuel transporting vessels or tanks contributes to the Gross Vehicle Weight (GVW).

The heavier a vehicle the more force that is needed to propel it, to stop it and the less weight it can carry.

Storage of gaseous fuel cylinders/tanks in a tractor or trailer must meet crash safety requirements. Tank cylinders are measured in terms of burst pressure. If a cylinder has a 3000 psi rating it will have a burst strength (or failure rating) of 2-3 times that normal 3000 psi rating.

Gross Vehicle Weight Rating (GVWR). This is the rating that is calculated by the manufacturer as the amount of weight that the vehicle will be when the vehicle itself is weighed filled with fuel and loaded according to the manufacturer's specification.

Highway Weight. This is the legal weight related to highway size and weight limits. When operating on the interstate system, the maximum permissible weight is 20,000 lbs. on a single axle, 34,000 lbs. on a tandem axle, and 80,000 lbs. max gross weight. The "Bridge Formula" allows motor vehicles to be loaded to the maximum weight only if each group of axles on the vehicle and their spacing also satisfy the requirements of the formula. States must use these limits for their designated or national network highways. While the majority of the states use the federal bridge formula for all roads in their state, some do have a separate state formula for other state or county roads.

There is an ongoing balance between safety and weight with respect to pressurized fuel in motor vehicles Traditional methods of reducing tank weight have included using plastic lined tanks wrapped in fibers. These composite tanks weigh less than metal tanks but are more susceptible to damage from cuts, gashes and the like. Inspections of composite tanks for signs of damage are necessary but can be costly and time consuming. Determining whether damage to a tank is minor or major is a difficult task traditionally accomplished by taking the tank out of service and inspecting and measuring the damage. The first decision is made by the customer who may not be experienced enough to judge if anything is wrong. This lack of experience may result in hazardous situations.

Additionally, if a tank is to be used on a motor vehicle it must meet additional certifications such as NGV-2 certification. One requirement is that a tank is required to pass flaw test. The flaw test consists of a 1 inch long and minimum 0.05 inch deep cut in the tank and another one 8 inch long and minimum 0.03 inch deep.

DISCLOSURE

Briefly, gaseous fuel storage cylinders add weight to vehicles. Weight affects capacity to carry load, cost to operate and regulatory issues.

Cylindrical pressurized filament wrapped composite cylinders are a light weight alternative to metal tanks for storing pressurized gaseous fuels. Such cylinder can withstand hoop and axial stresses applied externally of at least a quantity equal to the burst rating.

Where traditional filament wrapped tanks have failed is with respect to ease of inspection for damage. Aspect of the disclosure provides at least one of a novel and improved method, system and device to inspect composite pressurized tanks for external damage.

Disclosed herein is a fuel tank having a color indicator which corresponds to the level of damage due to tears, gashes, cuts and the like. The color indicator is part of a system and method to visually inspect tank damage and the extent of repair necessary.

In some instances a color band is positioned about 0.045 inches below the outer surface of the tank. In other instances the color band is positioned about 0.05 inches deep from outer surface of a composite tank. In some instances a first color band is positioned less than 0.045 inches below the surface of a tank and a second color band is positioned about 0.05 inches below the surface of the tank. The color band may be a layer, it may be global and it may be localized on the tank.

Color bands may be formed via a specific placement of a colored layer of material during manufacture. The color of a band may correlate to a specific location and/or depth of the band. The material may be filament or other wrapping. Color bands may be formed by coating the tank wrapping filament. A non-exclusive list of material for a filament are carbon fiber, glass, Kevlar™ and the like, which may be used to construct the tank. By utilizing coated filaments at a known position in the winding construction a color band may be positioned in a preselected area at a predetermined depth from the external surface of the tank.

Color bands may be formed via a specific placement of a colored layer of resin (resin is used to bind the filaments to the tank structure during manufacturing). The resin can be colored using pigments and dyes. By placing the colored resin at a known position in the winding construction a color band may be positioned in a preselected area.

In some instances an entire section of the winding, corresponding to the area from a specific distance of about 0.045 inches below the external surface of a completed tank to the surface may be utilized. In such instance when a color "upper" layer is torn through at a distance greater than about 0.045 inches the color of the filaments at a lower level would be visible. Naturally, contrasting colors are preferred for use as a visual indicator.

Disclosed herein are aspects of a tank for storing gases having visual indication to identify damage to the composite pressurized tank. In some exemplary implementations, a tank having an input and output with a wrapped liner; the wrapped liner forming the tank having a first color band located between a first and second wrap zone. The tank may have an underzone below the first color band. The first color band is placed at a predetermined depth below the outer surface of the tank. In some instances a second color band may be placed between the first and second wrap zones but at a different depth. The color band may be contrasting to the tank wrapping colors. In some instance the first color band is positioned at one of about 0.5 inches and about 0.045 inches below the outer surface of the tank.

Disclosed herein are aspects of a tank for storing gases having visual indication to identify damage to the composite pressurized tank. In some exemplary implementations a tank having an input and output with a wrapped liner; the wrapped liner forming the tank having a first color band located between a first and second wrap zone. The wrap zones include filaments or strips in an epoxy, resin or curable adhesive. The tank may have an underzone below the first color band. The first color band is placed at a predetermine depth below the outer surface of the tank. In some instances a second color band may be placed between the first and second wrap zones but at a different depth. The color band may be formed of filaments which are coated with a chemical coating which when illuminated by a specific range of wavelengths of light of the correct size emit a color. The color band may be contrasting to the tank wrapping colors. In some instance the first color band is positioned at one of about 0.5 inches and about 0.045 inches below the outer surface of the tank. In some instances the color band is a region of epoxy, resin or adhesive which contains a dye or pigment at the appropriate depth which corresponds to a predetermined alert threshold for damage.

Disclosed herein are methods of visual identification of damage to a composite pressurized tank. Aspect of exemplary implementations include visually inspecting the outer surface of a tank for color of a color band; and, if color is identified determine the extent of the damage and if it is less or greater than a threshold amount. If the threshold level is surpassed then remove the tank from service if damage exceeds a threshold. If the threshold level is not surpassed then repair the tank damage.

Disclosed herein are methods of visual identification of damage to a composite pressurized tank. Aspect of exemplary implementations includes visually inspecting the outer surface of a tank for color of a color band; wherein if the visual inspection includes determining the color of the color band and correlating the color to the depth of the damage.

Disclosed herein are methods of visual identification of damage to a composite pressurized tank. Aspect of exemplary implementations include visually inspecting the outer surface of a tank for color of a color band; and illuminating the tank with a specific wavelength of light which will cause any exposed color band to luminesce.

DRAWINGS

The above-mentioned features of the present disclosure will become more apparent with reference to the following description taken in conjunction with the accompanying drawings wherein like reference numerals denote like elements and in which.

Appendix "A" are photographs of tanks and damage indication.

While the specification concludes with claims defining the features of the present disclosure that are regarded as novel, it is believed that the present disclosure's teachings will be better understood from a consideration of the following description in conjunction with the appendix, figures, in which like reference numerals are carried forward. All descriptions and callouts in the Figures and appendix are hereby incorporated by this reference as if fully set forth herein.

FURTHER DESCRIPTION

According to one or more exemplary implementations, as shown in FIGS. 1-7, disclosed are aspects of a color indicator to asses, determine, view or locate damage to a composite fuel tank 10. The indication system allows a visual observation of the extent of a cut, gauge, tear or other damage whereby an assessment may be made on what, if any, repair is needed or whether the tank needs to be removed from service.

Figure 1:
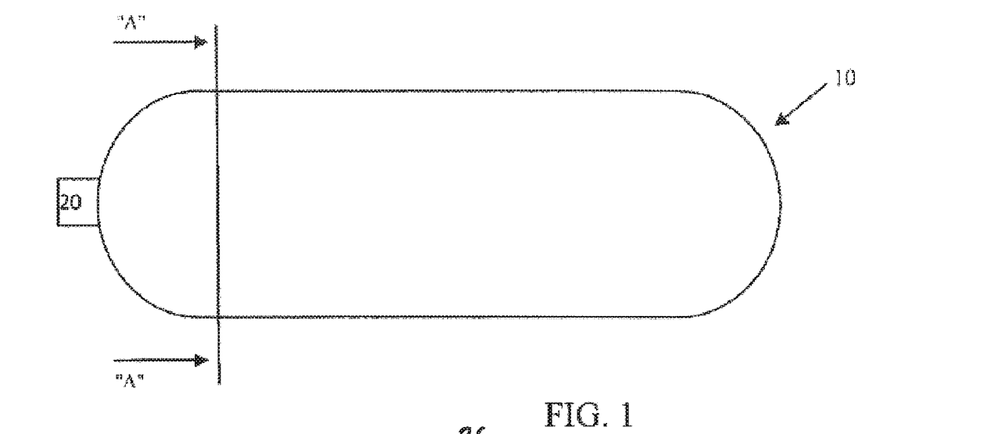
FIG. 1 is an external view of a composite fuel tank.
Figure 2:
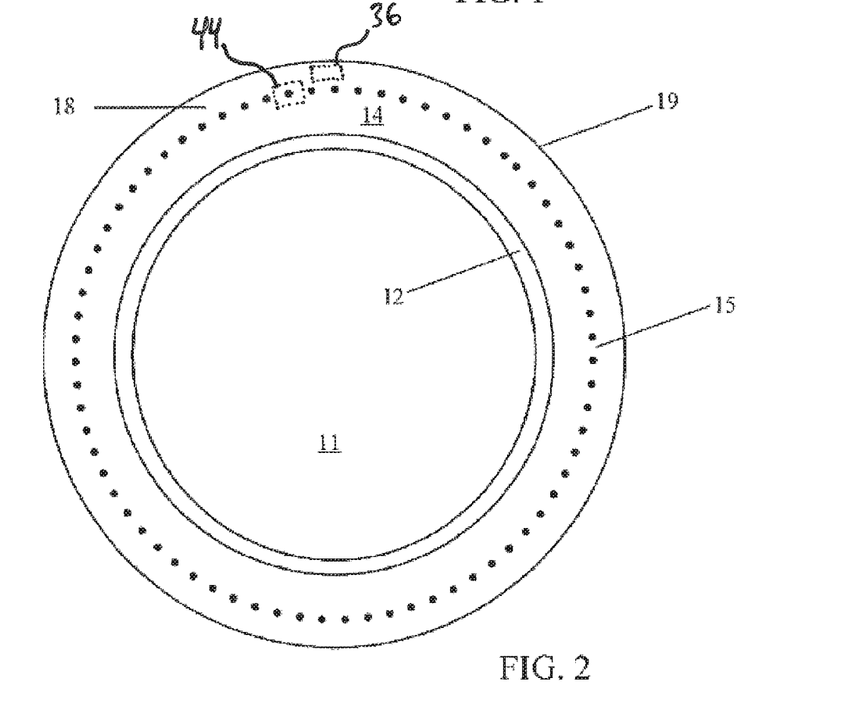
FIG. 2 is a cut-away view of FIG. 1 along line A-A.

Composite tanks illustrated have a volume 11 within an inner liner 12, a first wrap zone 14 of composite material and binding agent which may be one or more of localized, hoop wound and helically wound, a color band 15 and a second wrap zone 18 and input/output end 20. The wrapping process is a winding wherein a weave, braid or fabric like filament or strip of material is bound with a resin, epoxy or other curable adhesive to form the pressure bearing cylinder. Second wrap zone 18 is formed of a first underzone 36 and a second underzone 44, with the first underzone 36 being nearer to the external surface 19 of the tank 10 than the second underzone 44, within which the color band 15 is disposed.

The color band is a layer within the wrapped structure of filaments or strips forming the tank. The color band or layer should have a contrasting color from the wrappings. The layer may be a winding with several wraps. The color band fiber or strip may be coated with a material which when illuminated by wavelength of the correct size emits a color (luminescence). The coating may be referred to as a luminescing chemical. The layer may be reflective wherein it reflects light at a greater amount than the surrounding wrappings. The material of the color band may be coated with UV sensitive dye, so that it is easily visible in UV light or black light.

A layer, in some instances, is positioned about 0.045 inches below the outer surface of the tank. In other instances the color band/layer is positioned about 0.05 inches deep from outer surface of a composite tank.

Figure 3:
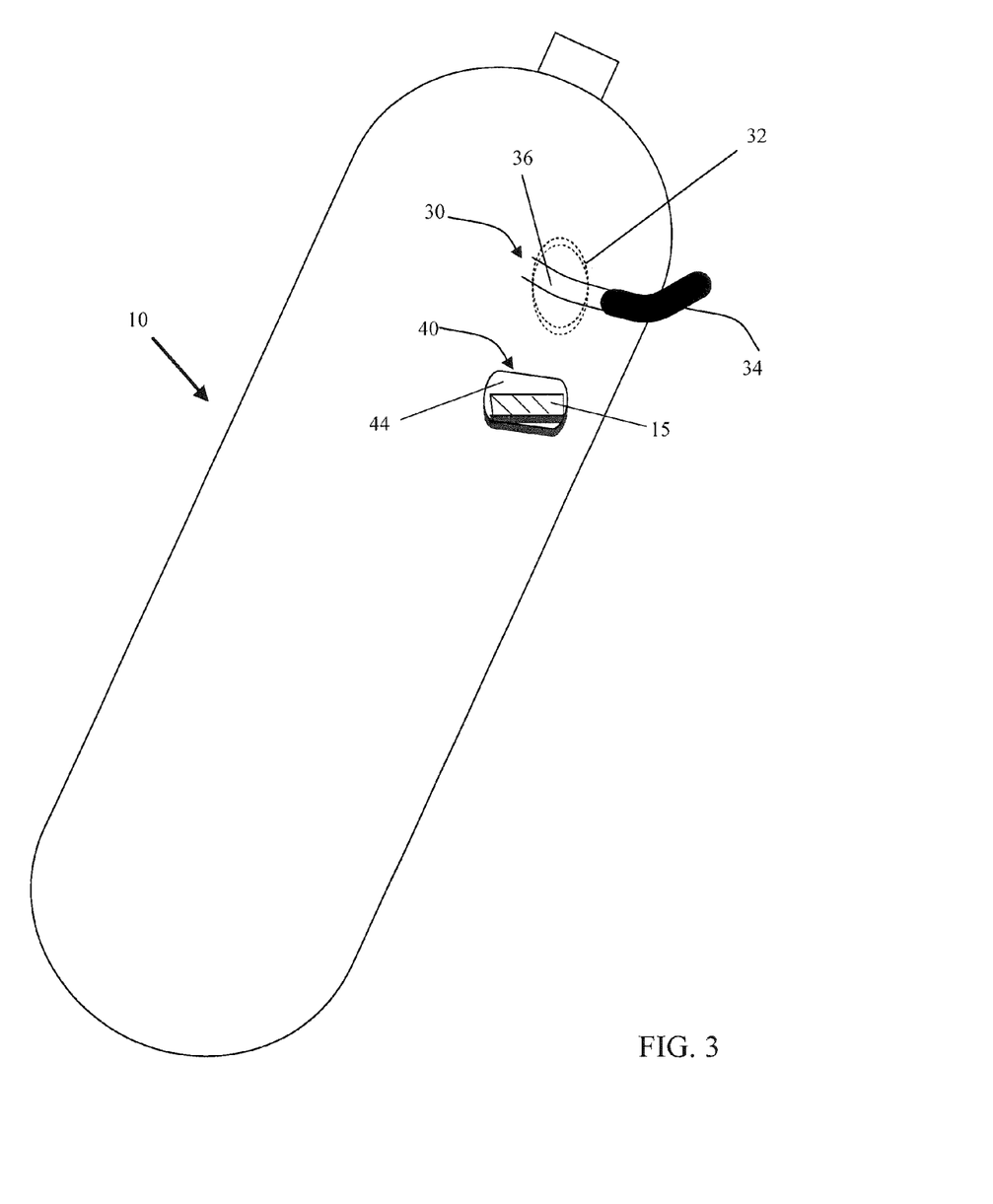
FIG. 3 is an external view of a composite fuel tank of FIG. 1 showing damage indication.

FIG. 3 illustrates a tank 10 with a first external damage 30 and a second external damage 40. In the first damage region 32, a portion of wrap 34 from the second wrap zone 18 has been pulled off revealing a first underzone 36 in the second wrap zone 18. That first underzone shows no color band 15 and may therefore, during a visual inspection, be evaluated consistent with the lack of a color band. The color band visualization may also be used in concert with other inspection methods as a factor in determining if a tank may be used as is, can be field repaired, or needs to be removed from service and repaired, or removed from service.

Figure 4:
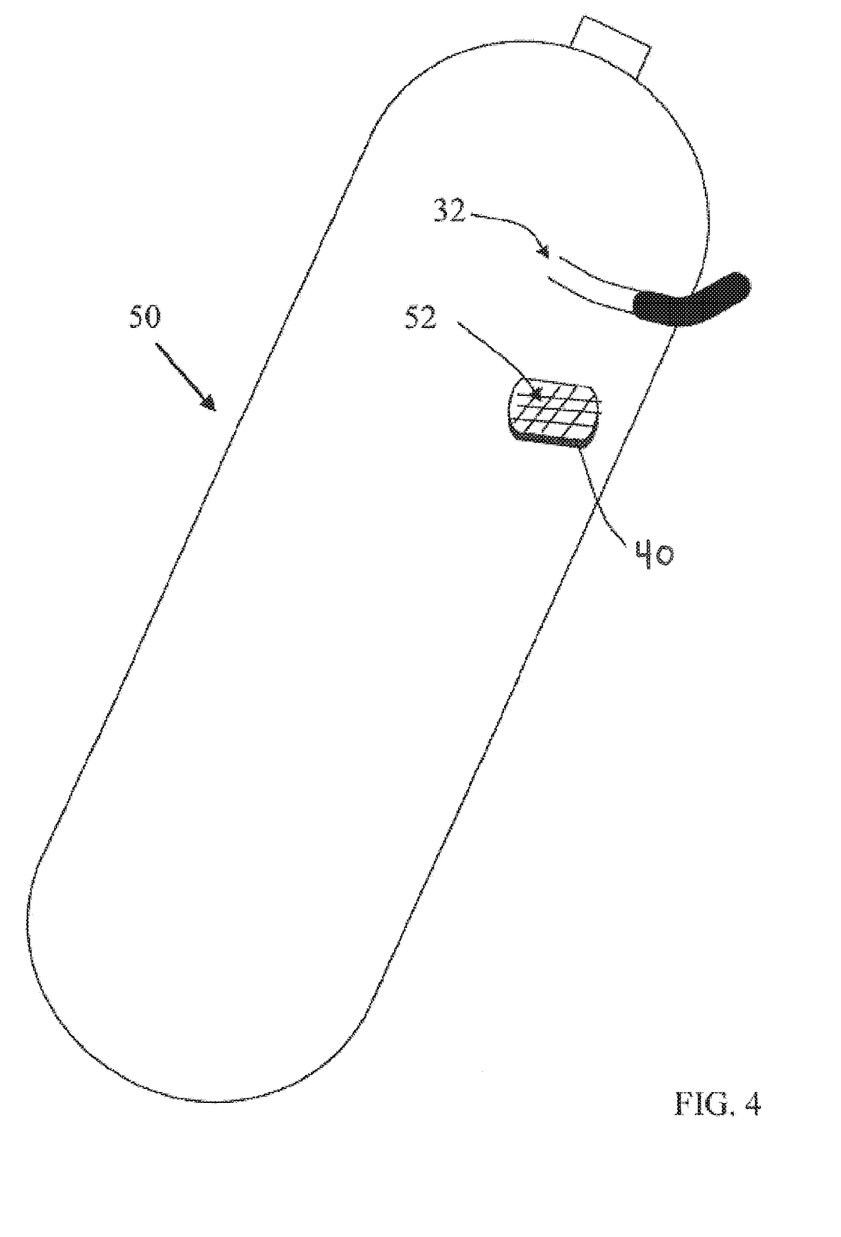
FIG. 4 an external view of a composite fuel tank showing damage indication.

In the second damage region 40 a gash reveals a second underzone 44 in the second wrap zone 18. That second underzone shows a portion of the color band 15. The visual inspection (which may be aided with specific wavelength lights or other lights) provides visual feedback of a flaw on the tank which is beyond the threshold level which the color band indicates. The threshold level may be adjusted during the manufacturing process via the placement of the color band. In some instance the placement (or depth) of the color band may correspond to a tanks usage. For instance in some instances the nearer to the external surface 19 of the tank 10 the color band is positioned the less depth tolerance that tank will have for a gash or tear. In other words if the color band is 5 mm from the external surface 19 versus 25 mm then a shallower gash or tear would indicate a threshold level of damage in the first instance but not in the second instance. The placement of the color band is predetermined by the tanks manufacture and applicable codes and guideline for the use of composite pressure vessels. The placement of the color band(s) may also reflect the nominal operating pressures of the tank. A tank operating at a higher burst pressure may be more susceptible to a shallow gash as opposed to a tank operating at a lower burst pressure. FIG. 4 shows another composite tank 50 with color band indicator. A mesh or netting 52 material is placed in a preselect location (depth) during the winding/wrapping process. When a gash or cut of sufficient depth occurs in the external surface 19 of the tank, such as second damage region 40 the netting may be seen as the color band during a visual inspection. A white color has the most contrast against carbon fiber black background which is often a tank wrapping material. The layer may be an open mesh (leno weave patterns) to allow for resin to flow through the material during the winding process also referred to as wrapping. The netting is place around the tank during winding to separate the first and second wrapping zones and create the color band.

Aspects of methods of inspection disclosed herein include visually inspecting a composite pressurized fuel tank for damage to its surface. If one or more color bands are visually identified, determine the extent of any damage. If damage exceeds a threshold value remove the tank from service or send in for repair. If the damage does not exceed the threshold do one of repair in the field and do nothing.

Aspects of methods of inspection disclosed herein include visually inspecting a composite pressurized fuel tank for damage to its surface. If one of a plurality of color bands is visually identified, determine the extent of all damage. If any damage exceeds a threshold value remove the tank from service or send in for repair. If all damage does not exceed the threshold do one of repair in the field and do nothing.

Those of ordinary skill in the art will recognize that there are many optional materials and schemes for placing a color or other visual indication band at certain level (depth) in a composite tank structure. Options which are within the scope of this disclosure include, but are not limited to, colored resin when different color fibers are used for winding (other than black); The tank may be wound with different color fiber materials indicating a depth by color; tank may be wound with different types of fabric/material layers which can be either coated or uncoated. The coated ones being coated with an indicator color; main fibers can be used (towpregs) with different types of color coating and coating for this purpose; Open meshes and closed mesh material may be used, the materials used for the meshes may be paper, plastic, glass, and the like; cylindrical fiber, fabric or mesh sleeves open at least one end may be slipped over a tank structure during manufacturer and that sleeve may have the indicator color thereon; and, layers of fiber may also be wound with a tracer tow added to the fiber bandwidth during winding process. Those of ordinary skill in the art will recognize that it is within the scope of this disclosure that a plurality of indicators may be formed in the same tank.

Figure 5:
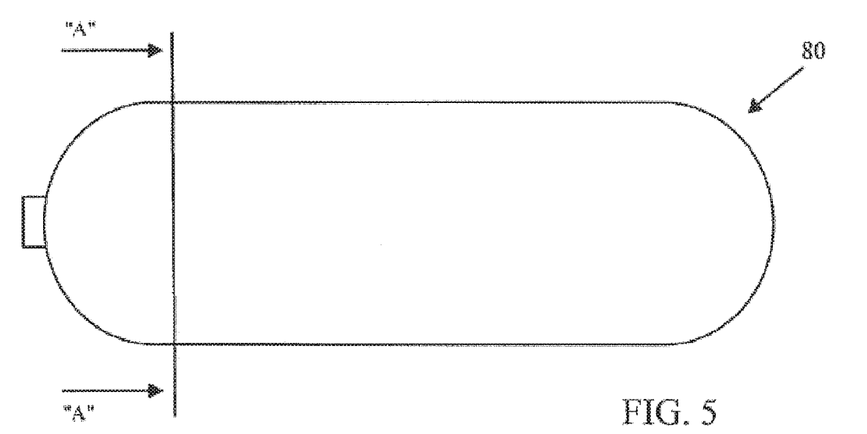
FIG. 5 is an external view of a composite fuel tank.
Figure 6:
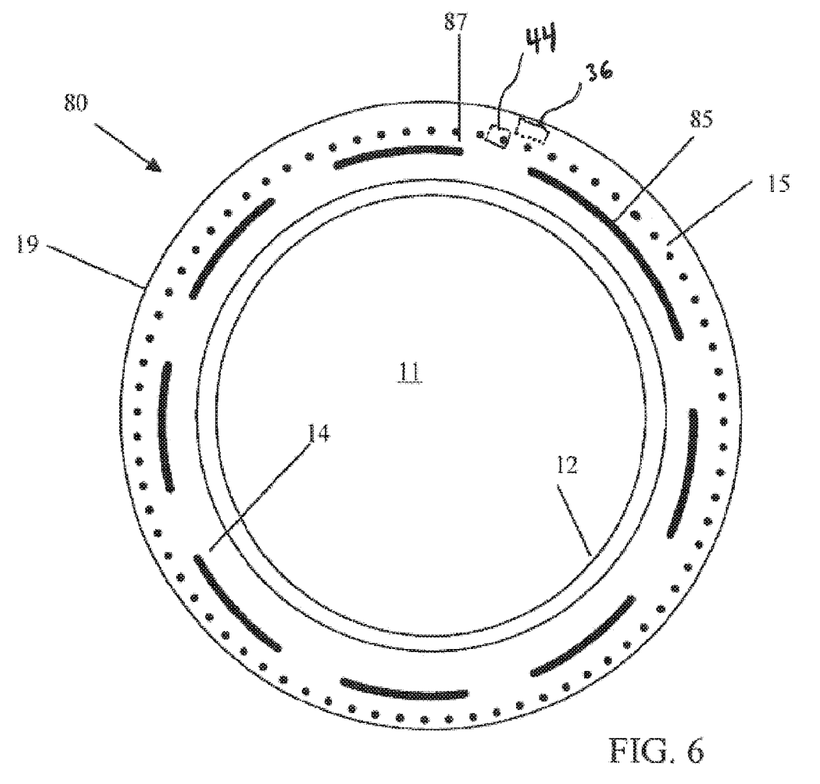
FIG. 6 is a cut-away view of FIG. 5 along line A-A.
Figure 7:
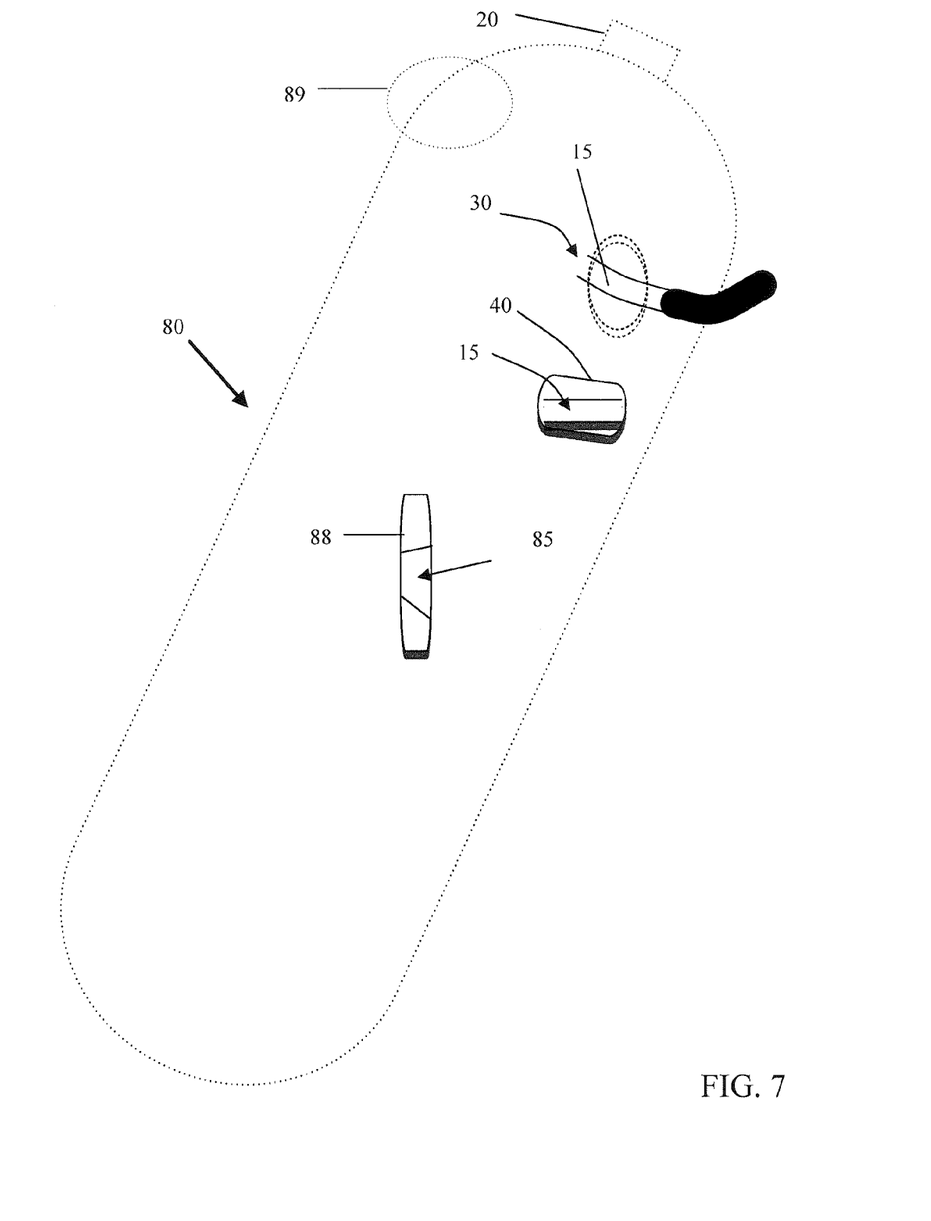
FIG. 7 an external view of a composite fuel tank of FIG. 5 showing damage indication.

FIGS. 5 through 7 show a composite tank 80 with at least two color band levels (different color or weave patterns or materials). The first color band 15 has been described above. A second color band 85 is added. Between the color bands is an intermediary wrapping zone 87. In some instances the uses of multiple color bands provide additional indications of the depth of a gash or tear in a tank. The second color band is visible in tear or gash 88. The second color band is located further from the surface of the tank than the first color band 15. Whereby the first color band may be a visual indicator of damage at a depth of "x" from the surface the second color indicator is indicative of a depth of "x+y".

Composite tanks may be more susceptible to shallow damage in certain areas 89. For those areas the color band material, or a localized placement of a portion of color band material, may be placed near to the surface 19 of the tank. In other instances the color bands may be placed at a substantially similar depth from the surface of the tank in other instance the color band may be at multiple depths to confirm the placement with the weak and stronger portions of the tank 10. Placement of damage indicator material is not limited to placement at depth corresponding to current NGV regulation. Placement of color bands may be at any predetermined level(s). In some embodiments, such as the non-limiting embodiment shown in FIG. 7, the area 89 may be disposed on a hemispherical end portion of the cylindrical composite tank 80. In some embodiments, the area 89 may be disposed on the hemispherical end of the cylindrical composite tank 80 nearest the input/output end 20.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A composite fuel tank for storing a pressurized fuel comprising:
   a cylindrical tank (10) having a first hemispherical end, a second hemispherical end, and an external surface (19);
   an input/output end (20) disposed on the first hemispherical end;
   wherein the cylindrical tank comprises: a liner (12); a first wrap zone (14) disposed around the liner; and
   a second wrap zone (18) disposed around the first wrap zone;
   wherein the second wrap zone comprises a first underzone (36);
   wherein the second wrap zone further comprises a second underzone (44) having a first color band (15) disposed therein;
   wherein the first underzone is disposed nearer to the external surface of the tank than the second underzone; and
   a second color band (85) disposed further from the external surface of the tank than the second wrap zone; and an intermediary wrap zone (87) disposed between the second wrap zone and the second color band;
   wherein the second color band is of a color which contrasts with the wrap zone material in which it is disposed.

2. The tank of claim 1 wherein the first color band is of a color which contrasts with the second wrap zone.

3. The tank of claim 1 wherein the first wrap zone, second wrap zone, or both further comprises a wrapping material which is at least one of a filament or strip in at least one of a curable adhesive, epoxy and resin.

4. The tank of claim 3 wherein the filament or strips are at least one of weaves, braids or fabrics.

5. The tank of claim 3 wherein the filament or strips are at least one of mesh and netting.

6. The tank of claim 3 wherein the filament is coated and the coating when illuminated by wavelength of the correct size emits a color by the property of luminescence.

7. The tank of claim 6 wherein the coating is a chemical sensitive to UV light.

8. The tank of claim 1 wherein the first color band is positioned about 0.045 inches below the external surface (19) of the tank.

9. The tank of claim 1 wherein the first color band is positioned about 0.05 inches below the external surface (19) of the tank.

10. The tank of claim 1 wherein the second color band is positioned at a depth which corresponds to a pre-determined depth; and wherein that pre-determined depth is the depth of tank damage that requires the tank to be taken out of service.

11. The tank of claim 8 wherein the color band is a region of epoxy, resin or adhesive which contains a dye or pigment at the 0.045 depth.

12. The tank of claim 9 wherein the color band is a region of epoxy, resin or adhesive which contains a dye or pigment at the 0.05 depth.

* * * * *